United States Patent [19]
Bigler et al.

[11] Patent Number: 5,435,034
[45] Date of Patent: Jul. 25, 1995

[54] ELECTRIC TOOTHBRUSH

[75] Inventors: Michael Bigler, Ittigen; Edgar Hommann, Grossaffoltern, both of Switzerland; Scott Myerly, Alpharetta, Ga.

[73] Assignee: Bausch & Lomb Incorporated, Rochester, N.Y.

[21] Appl. No.: 316,767

[22] Filed: Oct. 3, 1994

Related U.S. Application Data

[63] Continuation-in-part of Ser. No. 98,977, Jul. 28, 1993, Pat. No. 5,383,242.

[51] Int. Cl.[6] .................... A61C 17/34; A46B 13/02
[52] U.S. Cl. ............................................. 15/22.1; 74/57
[58] Field of Search ................. 15/22.1, 22.2, 22.4; 74/57; 310/50

[56] References Cited

U.S. PATENT DOCUMENTS

| | | | |
|---|---|---|---|
| 764,470 | 7/1904 | Jones et al. | 74/57 |
| 793,587 | 6/1905 | Johnson . | |
| 1,134,047 | 3/1915 | Hunter | 15/22.2 |
| 1,476,433 | 12/1923 | Vandervoot . | |
| 1,712,579 | 5/1929 | Nichols . | |
| 1,792,358 | 2/1931 | Byers et al. | 15/22.2 |
| 1,795,098 | 3/1931 | Scadding | 15/22.1 |
| 1,869,991 | 8/1932 | White et al. . | |
| 1,945,616 | 2/1934 | Mastrud | 15/22.1 |
| 2,044,863 | 6/1936 | Sticht . | |
| 2,140,307 | 12/1938 | Belaschk et al. . | |
| 2,201,190 | 5/1940 | Mastrud . | |
| 3,104,405 | 9/1963 | Perrinjaquet . | |
| 3,160,902 | 12/1964 | Aymar . | |
| 3,400,417 | 9/1968 | Moret et al. . | |
| 3,489,936 | 1/1970 | Boyles . | |
| 3,562,566 | 2/1971 | Kircher . | |
| 3,577,579 | 5/1971 | Duve et al. . | |
| 4,156,620 | 5/1979 | Clemens . | |
| 4,274,173 | 6/1981 | Cohen . | |
| 4,408,623 | 10/1983 | Murray | 15/22.1 |
| 4,756,202 | 7/1988 | Kawamoto . | |
| 4,783,869 | 11/1988 | Lee . | |
| 4,827,550 | 5/1989 | Graham et al. | 15/22.1 |
| 4,974,278 | 12/1990 | Hommann . | |
| 4,989,287 | 2/1991 | Scherer . | |
| 5,142,723 | 9/1992 | Lustig | 15/22.1 |

FOREIGN PATENT DOCUMENTS

| | | | |
|---|---|---|---|
| 0221460 | 5/1987 | European Pat. Off. . | |
| 0254397 | 1/1988 | European Pat. Off. . | |
| 0357863 | 2/1989 | European Pat. Off. . | |
| 706260 | 2/1930 | France . | |
| 1166163 | 11/1958 | France | 15/22.1 |
| 2368854 | 5/1978 | France . | |
| 2578408 | 9/1986 | France | 15/22.1 |
| 524651 | 4/1931 | Germany . | |
| 2736286 | 12/1978 | Germany . | |
| 2838015 | 3/1979 | Germany . | |
| 1632386 | 4/1980 | Germany . | |
| 2940275 | 4/1981 | Germany . | |
| 3334841 | 4/1985 | Germany . | |
| 3341465 | 5/1985 | Germany . | |
| 3544256 | 6/1987 | Germany . | |

OTHER PUBLICATIONS

Muller, Prof. Dr. J., *Basic Terms of Deviations in Cam Gears*, U. of Rostock, Dept. of Agricultural Engineering, Report No. 11 of the KDT Working Group on Cam Gears.

*Primary Examiner*—Edward L. Roberts, Jr.
*Attorney, Agent, or Firm*—Katherine McGuire

[57] ABSTRACT

An electric toothbrush having separable handle and brush segments, a rotating motor shaft extending exteriorly of the handle segment, and a reciprocating toothed rack in the brush segment which engages and imparts a counter-rotating movement to a plurality of tufts on the brush head. A cylindrically shaped gear mounts to and is axially movable on the motor shaft when the brush and handle segments are attached together. First and second lifting cams configured as elliptical flanges lying in oblique planes are provided in radially spaced relationship on the exterior surface and interior bore hole of the gear, respectively. Respective first and second guide grooves are associated with the lifting cams and the reciprocal toothed rack whereby rotation of the gear generates a long stroke of the rack through the interaction of the first and second lifting cams and guide grooves.

14 Claims, 8 Drawing Sheets

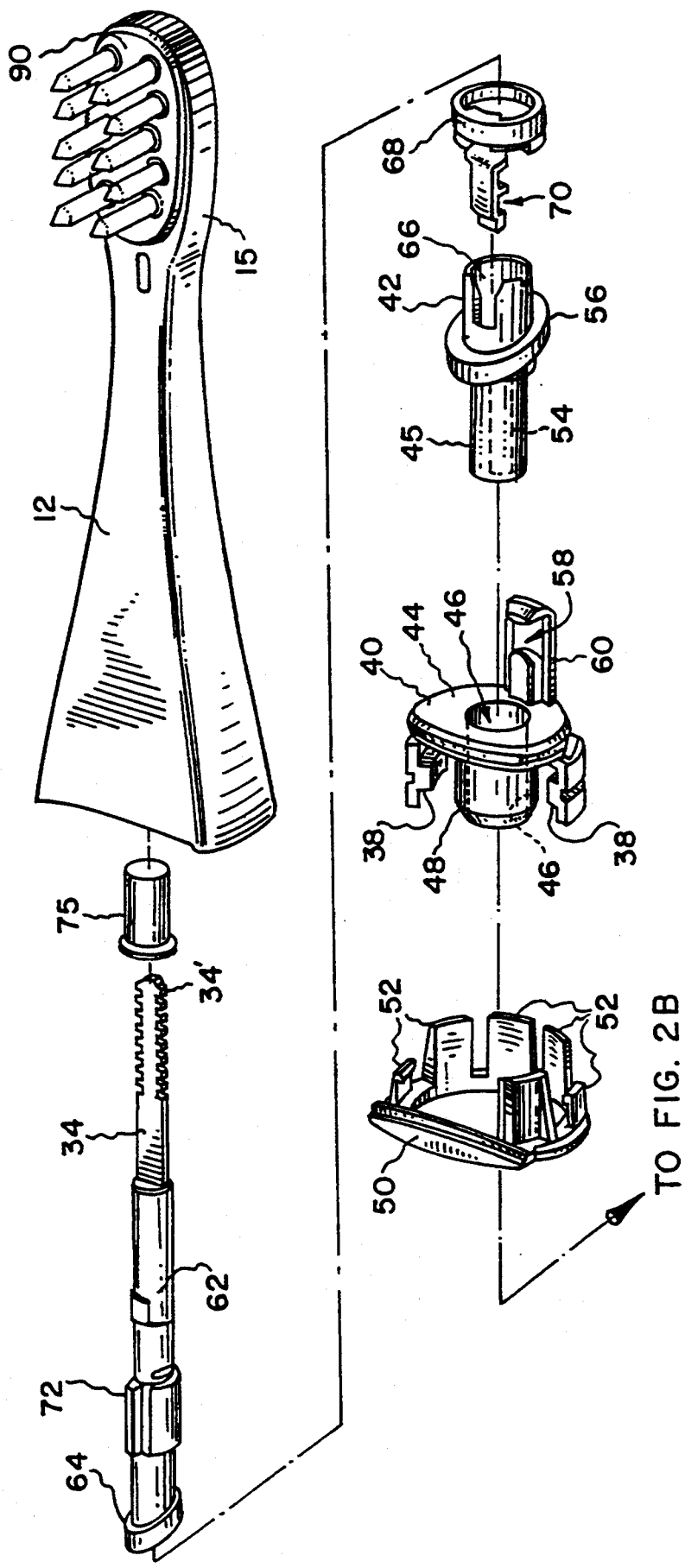

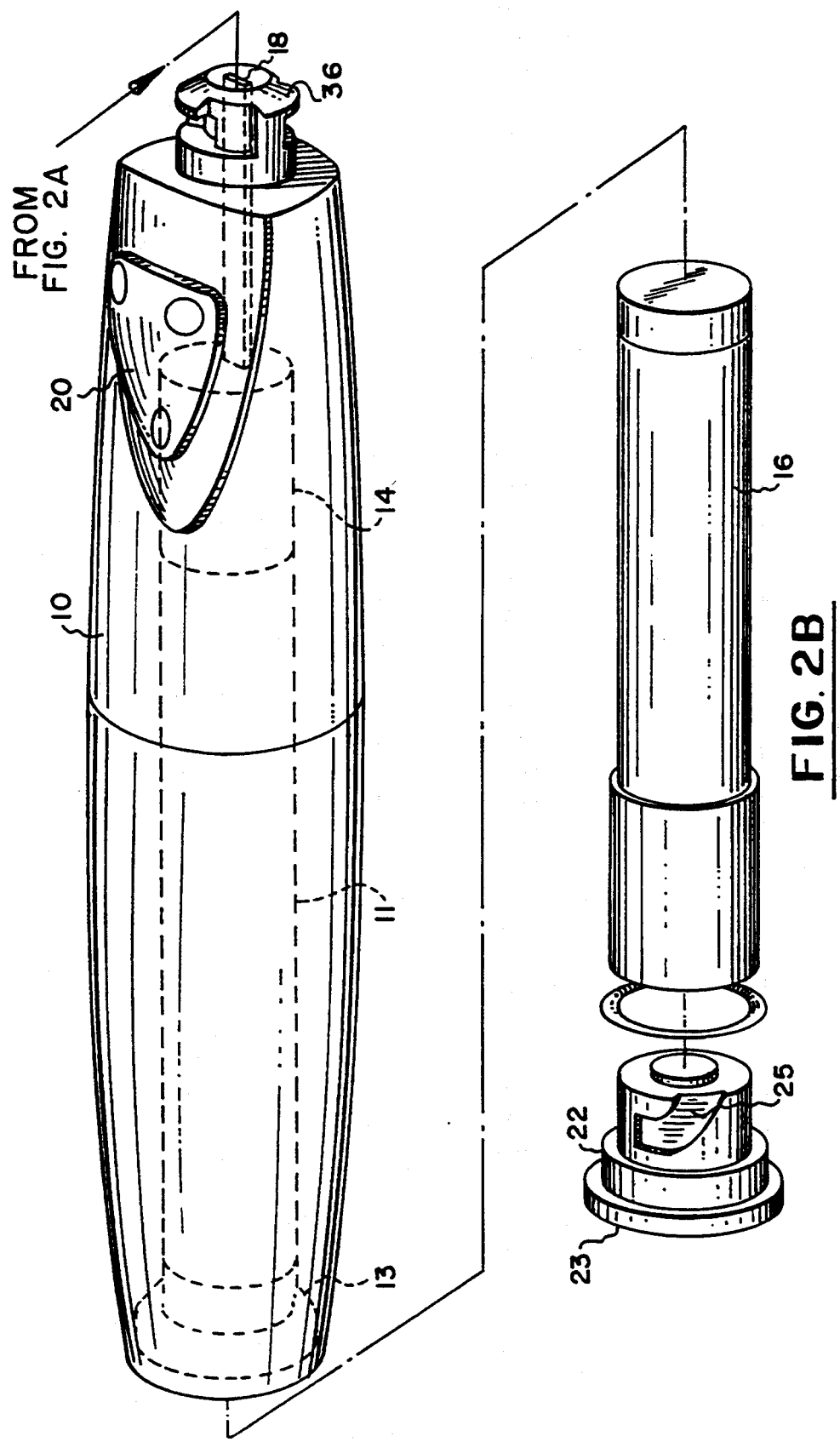

ELECTRIC TOOTHBRUSH

REFERENCE TO RELATED APPLICATION

This application is a continuation-in-part of U.S. patent application Ser. No. 08/098,977 filed on Jul. 28, 1993, now U.S. Pat. No. 5,383,242.

BACKGROUND OF THE INVENTION

The present invention relates to an electric toothbrush which has a revolving motor shaft, a gear that converts the motion of rotation into a reciprocating stroke, and a slip-on brush which is removably attached to a handle segment. The gear connects to and imparts a reciprocating movement to a toothed rack disposed in the slip-on brush which, in turn, drives the rotatable tufts in the brush head.

Such an electric toothbrush is the subject matter of U.S. Pat. No. 4,827,550 issued to Graham on May 9, 1989, the entire disclosure thereof being incorporated herein by reference. The Graham toothbrush utilizes a bevel gear including an eccentric which is driven by a pinion of the motor shaft in the handle segment. A crank arm attaches the eccentric to a drive shaft which leads out of the handle segment. Thus, the eccentric and crank arm together translate the rotational movement of the gear to a reciprocating movement of the drive shaft. The drive shaft automatically couples with a toothed rack in the slip-on brush when said brush is slid on the handle segment. The reciprocating movement of the toothed rack imparted by the drive shaft generates in turn an alternating motion of rotation of the individual tufts in the brush head.

If one wants to attain an adequately long stroke of the toothed rack, so that the bristle tufts execute more than one rotation at each stroke, the drive shaft leading out of the handle segment must execute an equally long stroke. Since the eccentric is offset on the bevel gear by half the stroke, the diameter of the bevel gear would have to be enlarged. The diameter of the handle segment which houses the gear would thus also have to be enlarged, yet large diameter handles are difficult to manually hold and work. The problem on which the invention is based is to design an electric toothbrush of the aforementioned kind in such a manner that its gear can be arranged to convert the rotation of the electric motor into a reciprocating motion of a long stroke in a toothbrush with a relatively small diameter.

SUMMARY OF THE INVENTION

This problem is solved by the invention in that the gear is configured as a cylinder which is set rotating by a revolving motor shaft of the electric motor. The gear is axially slidable on the motor shaft and is aligned in the longitudinal direction of the toothbrush. A lifting cam in the form of an elliptical flange extending in an oblique plane is provided on the exterior surface of the gear and is thus rotatable therewith. A stationary guide groove engages the lifting cam whereby the gear is caused to reciprocate along the motor shaft as it rotates. The toothed rack attaches to the gear such that the reciprocating movement of the gear results in a corresponding stroke of the toothed rack.

Such a gear has a small space requirement in the radial direction of the toothbrush, even though a large stroke is generated with it, because this stroke is generated by the course of the lifting cam. Arranging several lifting cams in succession further increases the stroke of the toothed rack to create a rotation of the tufts greater than 360°. This is accomplished while maintaining a minimum diameter of the toothbrush housing in that a second lifting cam can be provided in a bore hole formed in the gear. This radially spaced arrangement of the lifting cams acts to double the stroke length for every rotation of the gear. Despite this advantage, the toothbrush according to the invention is constructed very simply, so that it can be manufactured inexpensively with a low risk of malfunction.

Since the gear has a relatively small diameter, the gear may be easily disposed in the slip-on brush. The gear includes a coupling which automatically attaches the gear to the rotating motor shaft when the brush is attached to the handle. This is an especially advantageous embodiment in that the goal is reached that the gear, which has a tendency to wear, is no longer disposed in the handle segment. Thus, the gear is replaced automatically when the slip-on brush is replaced. Such a replacement of the slip-on brush takes place in any event from time to time, because the bristles are subject to wear due to the use of the toothbrush. Another advantage of this embodiment lies in the fact that only a rotating journal and not a reciprocating journal projects from the handle segment.

The toothed rack can be ensured not to rotate in a simple manner in that the outer shell of the toothed rack has at least one radially and longitudinally extending flange which engages with a longitudinally extending, grooved channel of the housing of the slip-on brush.

BRIEF DESCRIPTION OF THE DRAWINGS

FIG. 2A is an enlarged, perspective, exploded view of the slip-on brush and internal components thereof which include, among other things, the gear and toothed rack;

FIG. 2B is an enlarged, perspective view of the handle segment to which the slip-on brush of FIG. 2A attaches, with the battery and battery compartment cover shown removed from the handle;

DETAILED DESCRIPTION OF THE INVENTION

Figure 1:
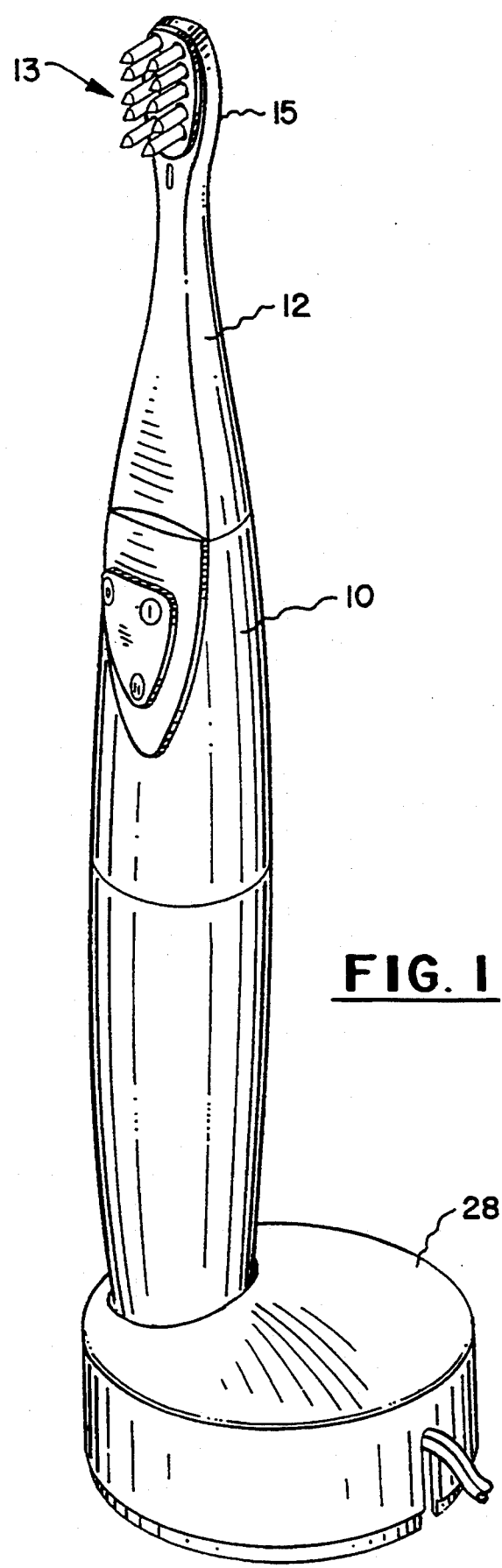
FIG. 1 is a perspective view of an electric toothbrush according to the invention shown mounted to a charging base.

FIG. 1 shows an electric toothbrush comprising substantially a handle segment 10 and slip-on brush 12 that carries a plurality of counter-rotatable tufts 13 on brush head 15. As seen in FIG. 2B, an electric motor 14 and removable battery 16 are disposed within handle segment 10, with motor 14 including a motor shaft having a non-circular terminal shaft end 18 extending therefrom to a position exteriorly of handle segment 10. A three-position switch 20 is provided on the handle segment 10 to operate motor 14 which sets motor shaft end 18 rotating.

Figure 4:
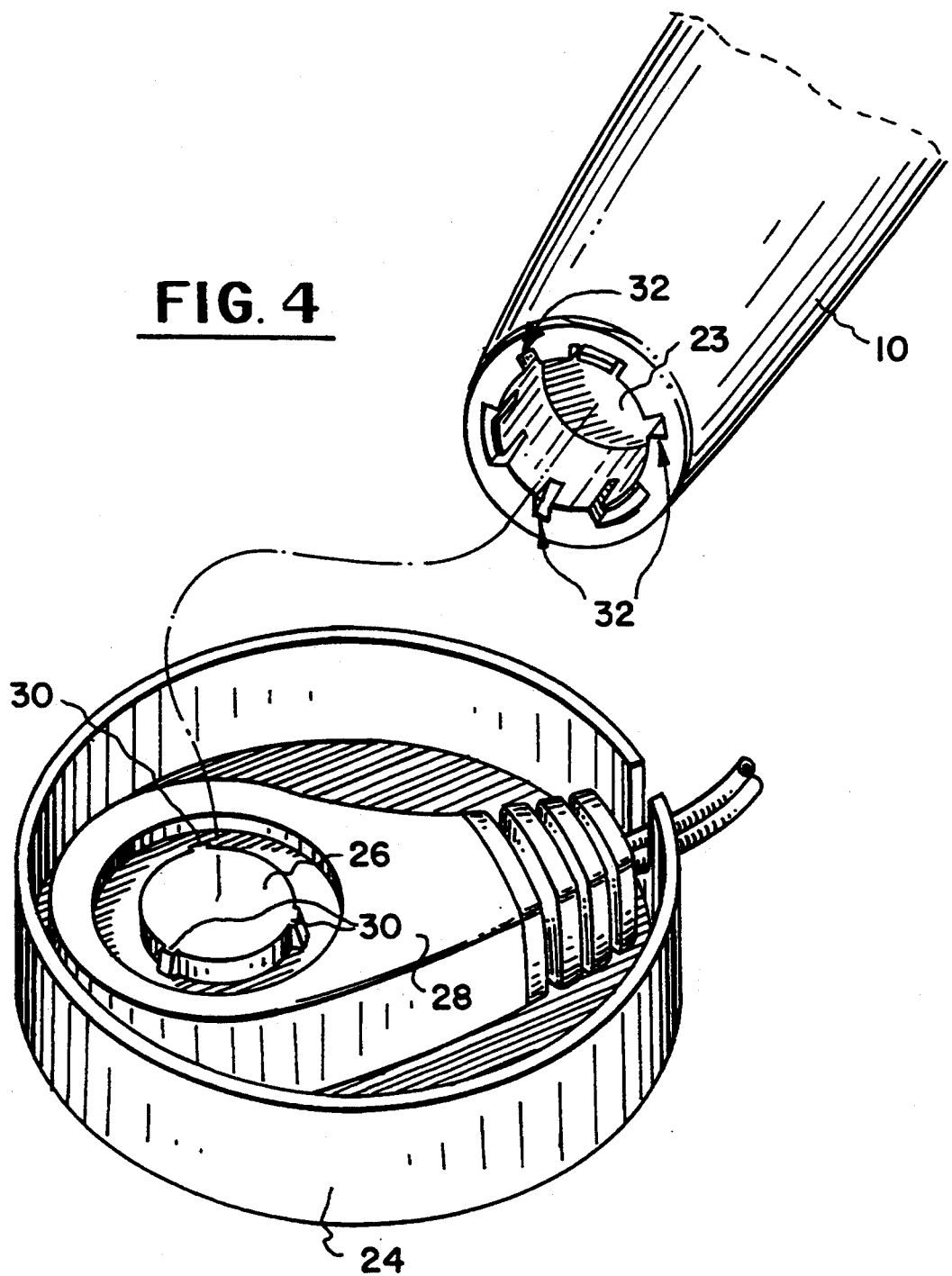
FIG. 4 is a fragmented, perspective view of the battery compartment end of the handle segment shown in spaced relation to the bottom surface of the battery charger which incorporates a battery cover removal tool thereon.

Battery 16 is held within the internal cavity 11 of handle segment 10 by a removable cover element 22. Cover 22 includes a recessed end 23 (FIG. 4) for mounting the electric toothbrush upon a peg-type inductive charging base 24 seen in FIG. 1. Cover element 22 further includes a curved notch 25 (FIG. 2B) for rotatably securing element 22 to handle segment 10 by engaging notch 25 with a lug (not shown) formed on the inner shell of the open end 13 of handle segment 10. As seen in FIG. 4, removal and attachment of cover element 22 is facilitated by the provision of a circular, wrench-type tool 26 which is integrally formed on the bottom surface 28 of base 24. Particularly, tool 26 includes a plurality of annularly spaced lugs 30 which may be placed in mating engagement with a respective plurality of annularly spaced notches 32 formed on the inner circumference of recessed end 23 of cover element 22. With the cover element 22 and tool 26 so engaged, rotating handle segment 10 easily and quickly releases/attaches element 22 from/to handle segment 10.

Discussion will first be directed to the means by which reciprocal rack 34 is set oscillating, and second to the gear arrangement of the tufts 13 which are set counter-rotating by the engagement and reciprocal movement of rack 34.

Figure 3A:
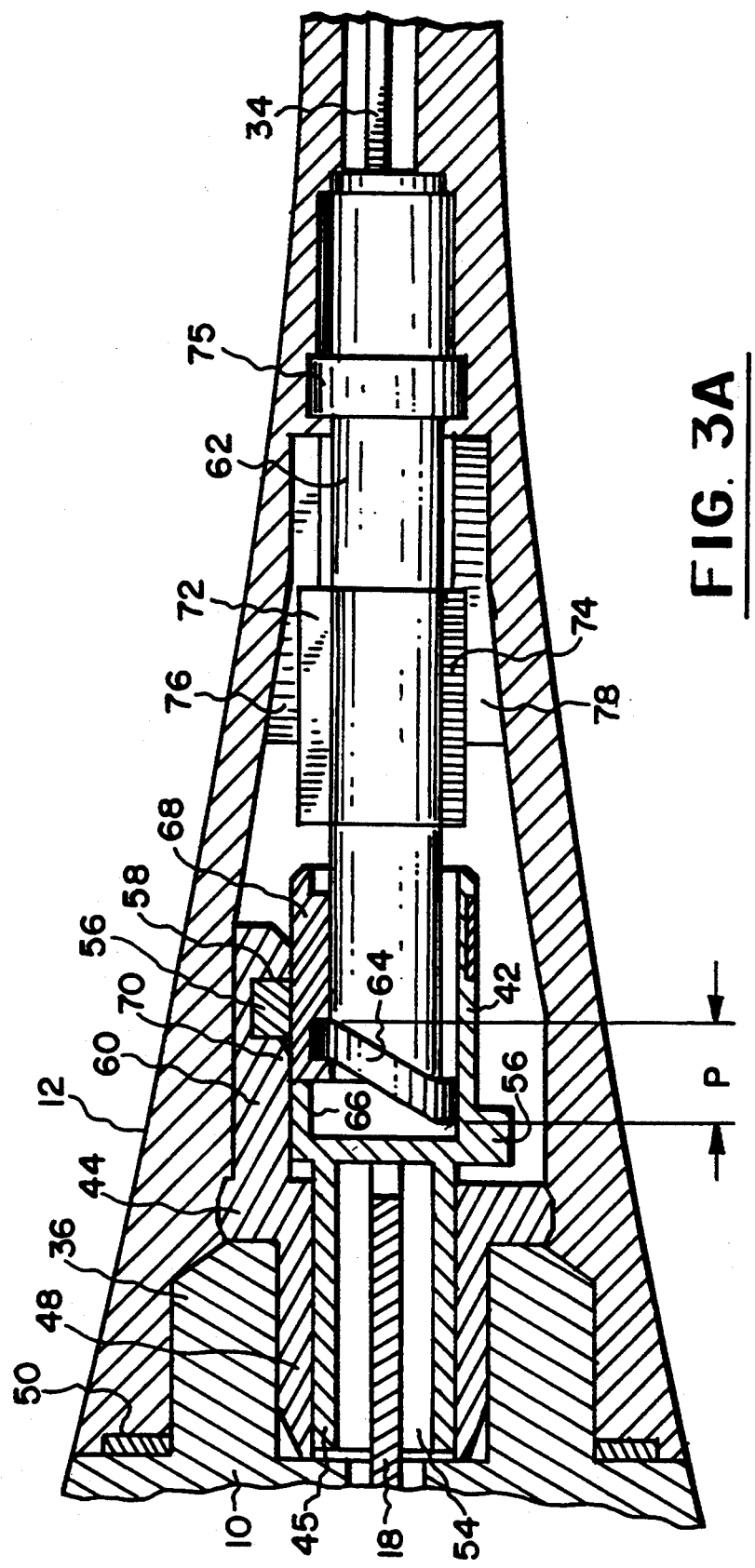
FIG. 3A is a fragmented, longitudinal, cross-section view of the handle segment and slip-on brush in the attached condition of FIG. 1 with the lifting cams shown in their fully retracted positions.
Figure 3B:
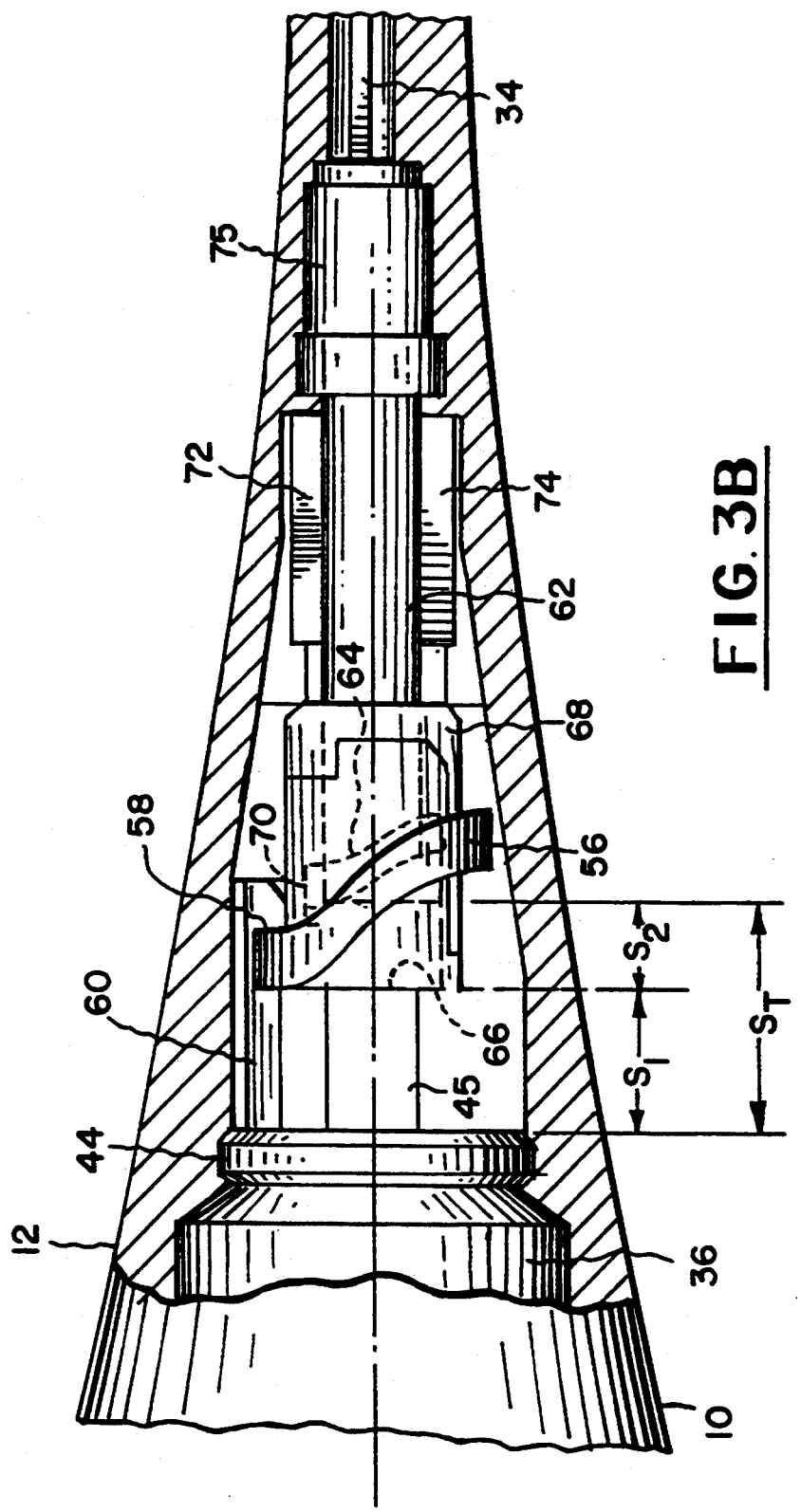
FIG. 3B is the view of FIG. 3A, with only selected parts shown in section, and with the first and second lifting cams shown in their fully extended positions.

Referring primarily to FIGS. 2A, 3A and 3B, slip-on brush 12 is hollow, forming an internal cavity wherein the rack-moving components of the brush are contained in the operably assembled condition of FIGS. 3A and 3B. Handle-to-brush releasable attachment means may take the form of bayonet-type connecting elements 36 and 38 respectively formed on the handle segment 10 (FIG. 2B) and a clip element 40 (FIG. 2A) which is held within the slip-on brush 12. Connecting element 36 is integrally formed with handle segment 10, extending therefrom in radially spaced relation to motor shaft end 18.

A gear 42 translates the rotation of the motor shaft end 18 into a reciprocating movement of toothed rack 34. Gear 42 is preferably configured as a cylinder including a motor shaft-coupling element 45, also configured as a cylinder, extending integrally and coaxially from gear 42. Clip element 40 serves the three-fold purpose of: 1) providing means (38) for securing brush 12 to handle 10; 2) axially locating gear 42 within the brush housing; and 3) providing means for imparting reciprocating movement to gear 42. No. 1 above was described in the preceding paragraph, and No. 3 above will be described below. With regard to No. 2 above, clip element 40 includes a locating ring portion 44 which includes a bore hole 46 wherethrough the coupling element 45 of gear 42 slidingly extends. Ring portion 44 also has an external perimeter which is shaped to fit in firmly abutting relationship to the inner surface of the brush housing, thereby securing both it and the gear 42 within the slip-on brush 12.

A cylindrical body portion 48 integrally extends from ring portion 44 in radially inwardly spaced relationship to connecting element 38, with bore hole 46 extending entirely therethrough for sliding passage of coupling element 45 of gear 42. As mentioned previously, motor shaft end 18 is non-circular, and is shown in FIG. 2B as being of a flattened, screw-driver type configuration. In this regard, coupling element 45 of gear 42 is provided with a slotted, cross-shaped passageway 54 which extends the entire length of coupling element 45. As such, when slip-on brush 12 is attached to handle 10 as seen in FIGS. 3A and 3B, motor shaft end 18 extends within passageway 54 so that coupling 45, and thus also gear 42, are rotatable thereby.

A color ring 50 is optionally provided at the end of brush 12 which includes annularly spaced fingers 52 for engaging between the inner wall of brush 12 and the outer surface of connecting element 38. Color ring 50 is used, for example, to distinguish between different slip-on brushes when more than one person is using the same handle segment 10.

Specific motion translation means takes the form of a first closed lifting cam 56 comprising an elliptical flange circumscribing the exterior surface of gear 42 in an oblique plane, and a guide groove 58 formed at the terminal end of a projection 60 extending perpendicularly from ring element 44 on the side thereof opposite cylinder portion 48. As seen in the assembled condition of brush 12 of FIGS. 3A and 3B, guide groove 58, which is rotationally stable with respect to the brush housing 12, engages lifting cam 56. Since cam 56 rotates with gear 42, rotation of gear 42 causes a corresponding oscillation thereof on and with respect to motor shaft end 18. In this regard, it is noted that passageway 54 and, hence, motor shaft end 18, are each of a length which is at least as long as the pitch P of lifting cam 56 (FIG. 3A). As such, cylindrical body portion 45 of gear 42 is able to slidingly reciprocate on motor shaft end 18 for each rotation of gear 42.

While the above-described components execute a first portion $S_1$ of the total stroke $S_T$ of toothed rack 34, a second lifting cam is additionally provided as described below which executes a second portion $S_2$ of the total stroke $S_T$ of toothed rack 34, where $S_1 + S_2 = S_T$ (FIG. 3B). Every stroke $S_T$ of toothed rack 34, which is caused by one full rotation (360°) of gear 42 as will be understood below, is effective at rotating each tufts 13 approximately one and a half turns (540°) before the tufts 13 begin their counter-rotating movement. A counter-rotating movement of the tufts 13 occurs when toothed rack 34 executes a consecutive return stroke $S_T$ in the opposite direction. Normally, such a large rotational movement of the tufts would require a lifting cam having an extremely long pitch which would be prone to locking. However, this objective is accomplished with the present invention through the provision of multiple lifting cams arranged in radially spaced fashion. This arrangement of the lifting cams minimizes the radial and longitudinal space requirements of the brush housing 12 which is a very desirable goal.

The execution of the first and second portions $S_1$ and $S_2$ of stroke $S_T$ is simultaneous. More particularly, the end of toothed rack 34 opposite toothed end 34' (FIG. 2A) colinearly attaches to a cylindrical shaft 62 which includes an angled terminal end forming a second lifting cam 64 arranged in an oblique plane to the longitudinal axis of shaft 62. The flanged perimeter of second lifting cam 64 interacts with gear 42 to generate the second portion $S_2$ of stroke $S_T$ as follows.

As seen best in FIGS. 2A, 3A and 3B, an axially extending bore 66 is formed in the end of gear 42 opposite cylindrical portion 45. A second clip member 68 forming a second guide groove 70 is affixed to gear 42 with guide groove 70 extending radially within bore 66 thereof. Since clip 68 is fixedly attached to gear 42 as described, clip 68, together with guide groove 70 thereof, rotates with gear 42. The end of shaft 62 opposite toothed rack 34 is inserted within bore 66 of gear 42 such that second guide groove 70 fully engages second lifting cam 64. To ensure that the toothed rack 34 does not rotate within brush housing 12, a pair of radially opposed fin elements 72 and 74 are provided on the shaft 62 which slide within respective grooved channels 76 and 78 formed on the inner surface of brush housing 12. As such, rotation of gear 42 and thus also second guide groove 70, engages second lifting cam 64 thereby causing a reciprocating movement of toothed rack 34 with respect to gear 42 identified by the second portion $S_2$ of the full stroke $S_T$.

A cam seal 75 is fixedly secured within brush housing 12 wherethrough toothed rack shaft 62 extends and slidingly reciprocates. Cam seal 75 is effective at preventing fluid from traveling from brush head 15 to the working components just described when the electric toothbrush is in use.

Figure 5:
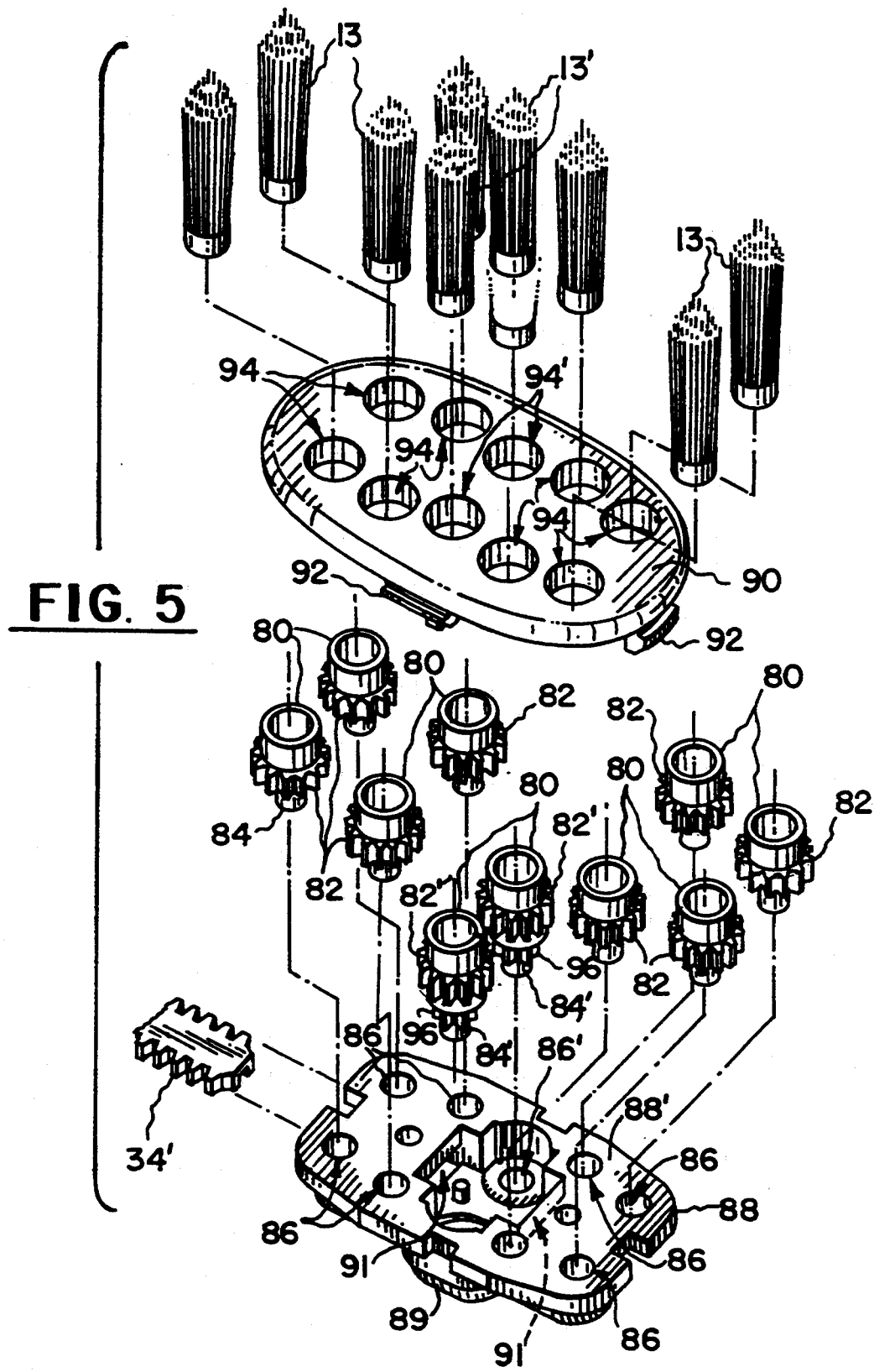
FIG. 5 is a partial, exploded, perspective view of the brush head portion of the slip-on brush showing the gear arrangement of the individual tufts in relation to the reciprocal rack (fragmented)
Figure 6:
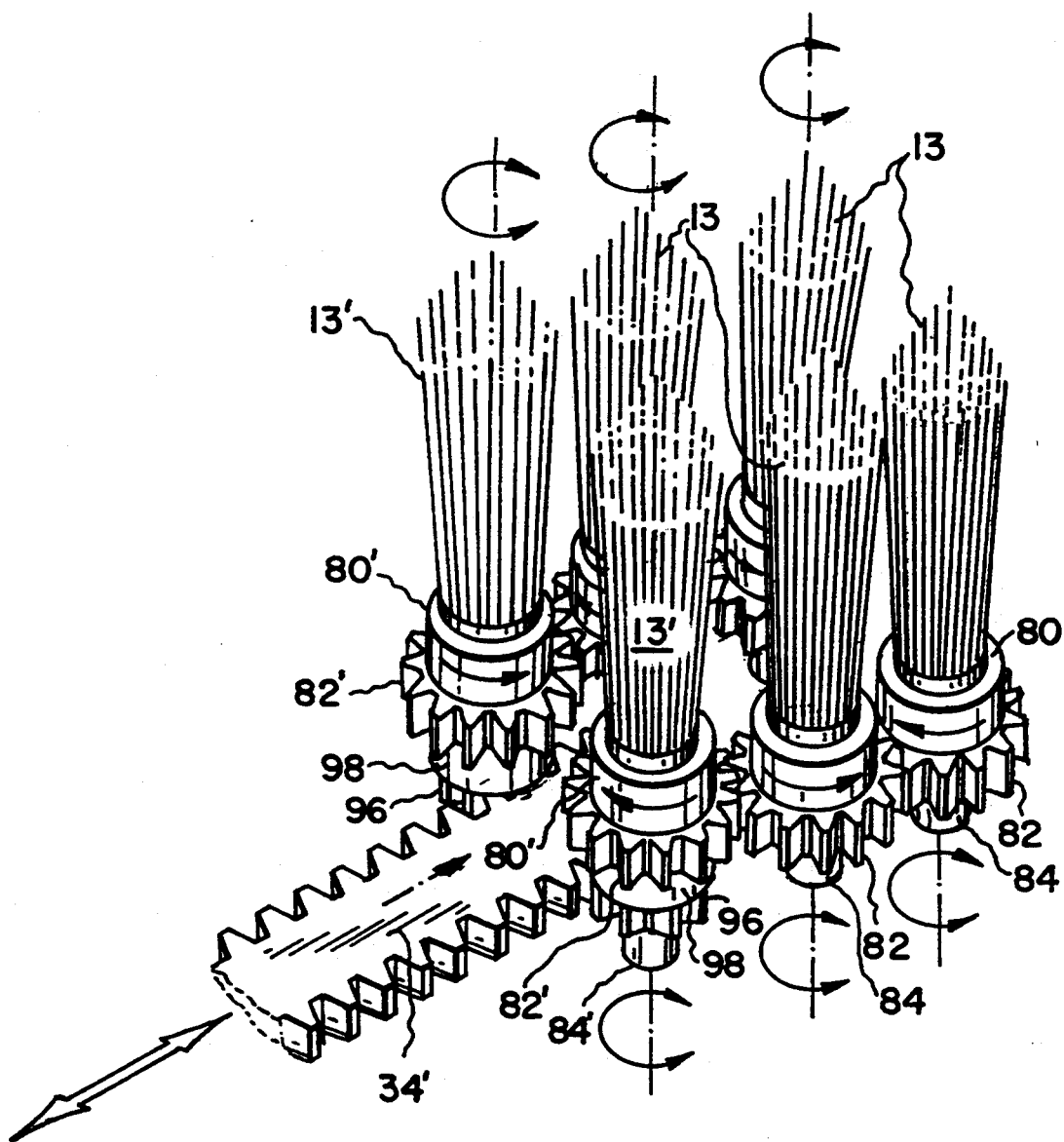
FIG. 6 is an enlarged, perspective view showing the reciprocal rack (fragmented) engaging the drive gears of the brush head with the four tufts located to the left of the drive gears in FIG. 6 not shown to improve clarity.

Lastly, attention is turned to FIGS. 5 and 6 which show the gear arrangement of the individual tufts 13 and the manner by which reciprocal toothed rack 34 sets tufts 13 into their counter-rotating movement. In the embodiment shown in the drawings, a total of ten tufts 13 are arranged on brush head 15 in longitudinally spaced, laterally adjacent pairs, although it is understood that any number of tufts may be installed for counter-rotating movement on brush head 15. Of the ten tufts 13 provided on brush head 15, only the center pair of tufts 13' are driven by toothed end 34' of reciprocal rack 34, with the remaining tufts 13 being set into counter-rotating movement through their connection with driven tufts 13' alone as set forth more fully below.

Tufts 13, 13' are fixedly secured to a respective tuft carrier 80, 80', each of which are provided with a spur gear 82, 82' encircling the circumferences thereof. A journal 84, 84' projects from each carrier 80, 80' opposite tufts 13, 13', respectively, which extend and are freely rotatable within holes 86, 86' formed in a bottom support plate 88 which is secured inside the hollow cavity of the brush head 15. A top cover plate 90 having catches 92 spaced about its perimeter is provided which snap fits to brush head 15 in covering relation to gears 82, 82', with tufts 13, 13' extending freely through a respective plurality of holes 94, 94' formed in top cover plate 90.

The carriers 80' of driven tuft pair 13' are further provided with drive gears 96 which directly engage toothed end 34' as seen in FIG. 6, with spur gears 82, 82' coaxially spaced thereabove within brush head 15. As seen in FIG. 5, bottom support plate 88 is provided with a counter-sunk center portion 89 wherein holes 86' are formed for receiving the journaled ends 84' of carriers 80'. Longitudinally spaced slots 91 are formed between center portion 89 and the upper planar surface 88' of bottom support plate 88 wherethrough toothed end 34' freely extends between and in meshing engagement with drive gears 96 of carriers 80'.

As seen best in FIG. 6, drive gears 96 and spur gears 82' are coaxially spaced apart from each other on their respective carriers 80' by a cylindrical segment 98. With ends 84' thereof journaled in holes 86' in center portion 89, cylindrical portion 98 spaces the bottom surface of the spur gears 82' thereof (which face away from top cover plate 90) to a position substantially flush with the upper planar surface 88' of bottom support plate 88. As such, spur gears 82' mesh with the longitudinally adjacent spur gears 82, the bottom surfaces of which lie on top of the upper planar surface 88' of bottom support plate 88.

Thus, in the fully assembled, working condition of brush head 15, rack end 34' and drive gears 96 extend below bottom support plate 88 while spur gears 82, 82' extend thereabove. Since spur gears 82' are fixed to carrier 80' as are respective drive gears 96 thereof, the counter-rotating movement of drive gears 96 caused by the reciprocating movement of rack end 34' causes a corresponding counter-rotating movement to spur gears 82', and thus also to remaining spur gears 82 by virtue of their longitudinally adjacent, inter-meshing arrangement.

It will be noticed that drive gears 96 are smaller in diameter and have fewer teeth than spur gears 82' (which are identical to the remaining spur gears 82). In the preferred embodiment, drive gears 96 are half the diameter and have half the amount of teeth than spur gears 82'. As such, carriers 80, 80' and associated tufts 13, 13' are caused to counter-rotate by an amount substantially larger than the linear displacement ($S_T$) of reciprocal rack 34 which, in turn, is dictated by the diameter of the gear 42 and shaft 62, and the pitch lengths of their associated lifting cams 56 and 64, respectively, both of which are desirably kept to a minimum due to the radial space constraints of the slip-on brush 12 and the threat of locking. In the preferred embodiment shown, drive gears 96 each have seven teeth and are approximately half the diameter of spur gears 82, 82' each of which have fourteen teeth.

We claim:

1. In an electric toothbrush having a housing divided into a handle segment and a slip-on brush segment releasably secured to the handle segment, the handle segment including an electric motor having a motor shaft revolving about a shaft axis lying parallel to the longitudinal axis of the toothbrush, the slip-on brush having a reciprocal toothed rack having first and second ends, said first end thereof engaging and imparting counter-rotating movement to a plurality of tufts on the head of the slip-on brush, wherein the improvement comprises:
   (a) a cylindrically shaped gear connected to the motor shaft so as to be rotatable therewith and axially movable relative thereto in the direction of said longitudinal axis, said toothed rack second end being attached to said gear;
   (b) a first lifting cam configured as an elliptical flange lying in an oblique plane with respect to said longitudinal axis; and
   (c) a first guide groove for engaging said first lifting cam, one of said first lifting cam and first guide groove being fixed with respect to said gear, and the other of said first lifting cam and first guide groove being fixed with respect to said toothbrush housing;

whereby the rotation of said motor shaft and said gear generates a first reciprocating stroke ($S_1$) of said toothed rack through the interaction of said first lifting cam and first guide groove.

2. The electric toothbrush of claim 1, wherein the improvement further comprises:
   (d) a second lifting cam; and
   (e) a second guide groove for engaging said second lifting cam, one of said second lifting cam and second guide groove being fixed with respect to said gear, and the other of said second lifting cam and second guide groove being fixed with respect to said toothed rack;
   whereby rotation of said motor shaft and said gear generates a second reciprocating stroke ($S_2$) of said toothed rack through the interaction of said second lifting cam and second guide groove, where ($S_1$)+($S_2$) equals the total reciprocating stroke ($S_T$) of said toothed rack.

3. The electric toothbrush of claim 2, wherein said first and second lifting cams extend in radially spaced relationship to each other.

4. The electric toothbrush of claim 3 wherein said gear includes an axially extending bore hole wherein said one of said second lifting cam and said second guide groove is positioned, said one of said first lifting cam and first guide groove being positioned on the exterior surface of said gear.

5. The electric toothbrush of claim 4 wherein said one of said second lifting cam and said second guide groove is attached to said toothed rack second end, whereby said toothed rack reciprocates relative to said gear during said second reciprocating stroke ($S_2$) of said toothed rack.

6. The electric toothbrush of claim 5 wherein said second lifting cam is configured as an elliptical flange lying in an oblique plane with respect to said longitudinal axis.

7. The electric toothbrush of claim 6 wherein said second lifting cam is fixed to said toothed rack second end, and said second guide groove is fixed to and radially extends within said gear bore.

8. The electric toothbrush of claim 7 wherein said first lifting cam is fixed to the exterior surface of said gear.

9. The electric toothbrush of claim 8 and further comprising a first clip member fixedly secured within said brush segment housing, said first guide groove being fixed to said first clip member.

10. The electric toothbrush of claim 9 wherein said first clip member is positioned between said motor shaft and said gear, and wherein a portion of said gear extends through a hole formed through said first clip member and engages said motor shaft.

11. The electric toothbrush of claim 10 and further comprising first and second coupling elements fixed to said handle segment and said clip member, respectively, wherein said first and second coupling elements may be brought into mating engagement to releasably secure said brush segment to said handle segment.

12. The electric toothbrush of claim 1, wherein the improvement further comprises:
   d) a plurality of spur gears to which said plurality of tufts are fixedly secured, respectively, each of said spur gears being of a first diameter and arranged in meshing engagement with an adjacent one of said spur gears;
   e) a drive gear fixedly attached in coaxially spaced relation to at least one of said spur gears, said at least one drive gear having a second diameter smaller than said first diameter, said toothed rack engaging and imparting counter-rotating movement to said drive gear which thereby imparts counter-rotating movement to said at least one spur gear and ultimately to each said spur gear arranged in said meshing engagement.

13. The electric toothbrush of claim 12 wherein said drive gear has half as many teeth as said at least one spur gear.

14. The electric toothbrush of claim 1 wherein said gear is disposed within said slip-on brush segment.

* * * * *